United States Patent [19]

Grimberg

[11] Patent Number: 5,151,270
[45] Date of Patent: Sep. 29, 1992

[54] SELF-EMULSIFIABLE DERMATOLOGIC CREAM

[76] Inventor: Georges S. Grimberg, 123 rue de l'Université, 75007 Paris, France

[21] Appl. No.: 443,407

[22] Filed: Nov. 30, 1989

[30] Foreign Application Priority Data

Dec. 2, 1988 [FR] France ............................. 88 15827
Jun. 15, 1989 [FR] France ............................. 89 07953

[51] Int. Cl.⁵ .......................... A61K 7/48; A61K 7/02
[52] U.S. Cl. .................................... 424/401; 514/844; 514/846; 514/847
[58] Field of Search ............. 424/401; 514/844, 846, 514/847, DIG. 5

[56] References Cited

U.S. PATENT DOCUMENTS 4,293,542  10/1981  Lang et al. ............................. 424/47
4,534,980  8/1985  Itoh et al. ............................. 514/570
4,581,230  4/1986  Grollier et al. ....................... 514/778

OTHER PUBLICATIONS

Barnett, G. "Emollient Creams and Lotions", *Cosmetics Science and Technology*, pp. 113 and 131.

*Primary Examiner*—Thurman K. Page
*Assistant Examiner*—Amy Hulina
*Attorney, Agent, or Firm*—Browdy and Neimark

[57] ABSTRACT

The cream comprises a mixture of sorbitan monosteaerate, polyoxyethylenated sorbitan monostearate, steraric acid, petrolatum oil, isopropryl myristate, triethanolamine, methyl parahydroxybenzoate, propyl parahydroxybenzoate, water (distilled or natural). The mixture is heated until the products are all melted and solubilized, and brought to a temperature between 80° C. and 120° C., for a period of time of 15 to 75 minutes. The mixture is then stirred while being left to cool down.

2 Claims, No Drawings

All the hereabove substances with exception of the fragrance are heated between 80° C. and 120° C. up to complete melting of the products, then the whole mixture, is stirred, and the fragrance is added at a temperature of about 40° C.

The product which is still in a liquid state is for example put into 10 ml ampoules. The product becomes then solid, and when the ampoule is stirred, the product becomes liquid again, and it is possible to recover it and to add thereto any suitable products.

By way of example, 10 ml of a perfumed cream contained in an ampoule with two points has been stirred very quickly. The cream became liquid. This liquid cream, poured into a dropper sprayer containing polymyxine, oxytetracycline, nystatin and dexamethasone has given, after agitation, a fluid product which, after a certain period of time became solid again.

Use of such a liquid-solid cream, which can be used not cosmetologically but pharmaceutically, has been studied for being placed in sinus and/or auricular cavities of patients. In its liquid form, the cream spreads on the mucusa and, with time, adheres to the mucosa by being solidified. The clinical results obtained have been excellent and have allowed treating many infections of the otolaryngological sphere.

In order to make the dermatologic cream of the present invention, a variety of ingredients can be used in addition to the ingredients described in the specific examples.

The oleaginous component can be any cosmetically acceptable oleaginous material that is compatible with the other ingredients used, such as calcium stearate, mineral oil, and the like.

The emulsifier can be any cosmetically acceptable emulsifier such as nonionic, anionic, and cationic emulsifiers, which are well known to those skilled in the art, with the proviso that the emulsifier used is compatible with the other ingredients in the cream.

Any known preservative that is cosmetically acceptable can be used in place of the methyl and propyl parahydroxybenzoate.

Conventional cosmetically acceptable components can be used in preparing the cream according to the present invention, which components are heated up to obtain a complete melting of the products at stirred at this temperature (80°-20° C.) for approximately 15 to 75 minutes, after which time the mixture is cooled with stirring.

I claim:

1. A self-emulsifiable, thixotropic dermatologic cream, produced by the following process:

first, mixing the following products at room temperature:

| | |
|---|---|
| Sorbitan monostearate | 8.55 g |
| Polyoxyethylenated sorbitan monostearate | 8.55 g |
| Stearic acid | 31.8 g |
| Petrolatum oil | 17.1 g |
| Isopropyl myristate | 42.0 g |
| Magnesian yeast | 4.0 g |
| Triethanolamine | 0.424 g |
| Methyl parahydroxybenzoate | 0.159 g |
| Propyl parahydroxybenzoate | 0.159 g |
| Distilled water | 283.5 g |
| Fragrance | 1.720 g | heating the mixture to a temperature between 80° C. and 120° C. for a period of time of 15 to 75 minutes, such that said products are all melted and solubilized; and allowing the mixture to cool down while stirring.

2. A self-emulsifiable, thixotropic dermatologic cream, produced by the following process:

first, mixing the following products at room temperature:

| | |
|---|---|
| Sorbitan monostearate | 4.65 g |
| Polyoxyethylenated sorbitan monostearate | 4.65 g |
| Stearic acid | 17.25 g |
| Petrolatum oil | 9.25 g |
| Isopropyl myristate | 23.25 g |
| Triethanolamine | 0.25 g |
| Methyl parahydroxybenzoate | 0.40 g |
| Propyl parahydroxybenzoate | 0.40 g |
| Distilled water | 4.40 g |
| Fragrance | Q.S.P. | heating the mixture to a temperature between 80° C. and 120° C. for a period of time of 15 to 75 minutes, such that said products are all melted and solubilized; and allowing the mixture to cool down while stirring.

* * * * *

SELF-EMULSIFIABLE DERMATOLOGIC CREAM

FIELD AND BACKGROUND OF THE INVENTION

All creams used in cosmetology as well as a majority of pharmaceutical pomades contain two phases, an aqueous phase and an oily phase. It is in particular the case of the facial hypoallergenic cream described in U.S. Pat. No. 4,375,480 whose preparation is carried out by mixing the two phases at a temperature between 70° C. and 40° C. under moderate stirring, this cream which is intended for the skin can also contain vitamin E.

OBJECTS AND SUMMARY OF THE INVENTION

The present invention more particularly relates to dermatologic cream the components of which are mixed at room temperature, then the whole mixture is heated up to a temperature which is convenient for a melting and solubilization of all the products, then the whole mixture is stirred and left to cool down, whereafter there is added at a relatively low temperature any suitable fragance and additive which is sensitive to heat.

It should also be noted that the hereabove mentioned basic cream can be completed with various fragrances and/or active products These various products are fragrances and/or active principles, for example simple or compounded yeasts such as a magnesian yeast, antibiotics, biological lyophilizates, as well as all products compatible with the basic cream and adapted for softening the skin, treating it or perfectly penetrating the system.

According to the invention, the following products are first mixed at room temperature:
Sorbitan monostearate
Polyoxyethylenated sorbitan monostearate
Stearic acid
Petrolatum oil
Isopropyl myristate
Triethanolamine
Methyl parahydroxybenzoate
Propyl parahydroxybenzoate
water (distilled or natural)

Then the mixture is heated until all the products are melted and solubilized, and then the mixture is brought to a convenient temperature between 80° and 120° C., and more especially between 100° C. and 105° C., for a period of time of 15 to 75 minutes, then the mixture is stirred while being left to cool down.

According to another feature of the invention, appropriate and heat sensitive fragrances and additives are added at a relatively low temperature between 25° C. and 50° C. and more especially between 35° C. and 40° C.

Various other features of the invention will become more apparent from the following detailed description.

DETAILED DESCRIPTION OF THE INVENTION

By way of example, the following formula is given

| | |
|---|---|
| Sorbitan monostearate | 8.55 g |
| Polyoxyethylenated sorbitan monostearate | 8.55 g |
| Stearic acid | 31.8 g |
| Petrolatum oil | 17.1 g |

-continued

| | |
|---|---|
| Isopropyl myristate | 42.0 g |
| Magnesian yeast | 4.0 g |
| Triethanolamine | 0.424 g |
| Methyl parahydroxybenzoate | 0.159 g |
| Propyl parahydroxybenzoate | 0.159 g |
| Distilled water | 283.5 g |
| Fragrance | 1.720 g |

All the hereabove substances, with exception of the fragrance, are heated up to complete melting of the products; the mixture is then subjected to stirring and the fragrance is added at a temperature of about 40° C.

In order to heat the mixture until all the hereabove mentioned products are melted and solubilized, the mixture has to be brought to a convenient temperature between 80° and 120° C., more especially between 100° C. and 105° C. for a period of 15 to 75 minutes, and then the whole mixture is stirred and left to cool down.

Appropriate heat sensitive fragrances and additives are added at a relatively low temperature between 25° C. and 50° C., and more especially between 35° C. and 40° C.

Generally, the heating period of time can be estimated as being ½ hour.

Such a cream used by application in the morning has been tested on a sample of ten women aged from 25 to 80 years old and on three men from 50 to 55 years old.

The obtained results are mainly remarkable from two view points:

1) the cream is perfectly tolerated and no overheating or inflammation reaction, even ocular, has been observed;
2) the cream softens the skin and reduces quite markedly the wrinkles. The three men of the sample have also used the cream before travelling on motorcycles over a distance of 150 to 450 kilometers. There again, the results have been excellent, and the skin remained flexible and not dehydrated.

Independently of its self-emulsifiable quality, the dermatologic cream according to the invention can be diluted so as to give a milk or a lotion by simple addition of water when the cream is cooled and stored. This dilution can also be carried-out in the hot state.

Moreover and independently of this self-emulsifiable quality and of this dilution possibility, the dermatologic cream according to the invention is, as a function of the quantities of products used, a thixotrope, meaning that when stirred, it becomes liquid again and then recovers its creamy aspect a certain period of time after stirring has stopped. It is therefore easy to incorporate again to this cream and under stirring other products extemporaneously, for example antibiotics, antimycosics and, once stirring has stopped, it becomes creamy again.

A preferred formula of a thixotrope cream according to the invention is as follows:

| | |
|---|---|
| Sorbitan monostearate | 4.65 g |
| Polyoxyethylenated sorbitan monostearate | 4.65 g |
| Stearic acid | 17.25 g |
| Petrolatum oil | 9.25 g |
| Isopropyl myristate | 23.25 g |
| Triethanolamine | 0.25 g |
| Methyl parahydroxybenzoate | 0.40 g |
| Propyl parahydroxybenzoate | 0.40 g |
| Distilled water | 440 g |
| Fragrance | sufficient quantity |

UNITED STATES PATENT AND TRADEMARK OFFICE
CERTIFICATE OF CORRECTION

PATENT NO. : 5,151,270
DATED : September 29, 1992
INVENTOR(S) : Grimberg

It is certified that error appears in the above-identified patent and that said Letters Patent is hereby corrected as shown below:

Column 4, Claim 1, line 15, delete
"- Fragrance ..................1.720 g"; and line 20, after the word
"stirring" insert --and then adding 1.720g fragrance--.

Column 4, Claim 2, line 14, delete "4.40" and insert -- 440 --;

line 15, delete
"- Fragrance..................Q.S.P."; and
                last line, after "stirring" insert
--and then adding fragrance--.

Signed and Sealed this

Eleventh Day of January, 1994

Attest:

BRUCE LEHMAN

Attesting Officer        Commissioner of Patents and Trademarks